(12) United States Patent
Chen et al.

(10) Patent No.: US 7,638,619 B2
(45) Date of Patent: Dec. 29, 2009

(54) VARIABLE REGION GENE OF HEAVY/LIGHT CHAIN OF ANTI-HUMAN HEPATOMA MONOCLONAL ANTIBODY HAB 18 AND USE THEREOF

(76) Inventors: Zhinan Chen, Cell-Engineering Researching Center of the Fourth Military Medical University, Xi'an, Shanxi Province 710032 (CN); Jinliang Xing, Cell-Engineering Researching Center of the Fourth Military Medical University, Xi'an, Shanxi Province 710032 (CN); Sihe Zhang, Cell-Engineering Researching Center of the Fourth Military Medical University, Xi'an, Shanxi Province 710032 (CN)

( * ) Notice: Subject to any disclaimer, the term of this patent is extended or adjusted under 35 U.S.C. 154(b) by 303 days.

(21) Appl. No.: 10/507,941

(22) PCT Filed: Mar. 17, 2003

(86) PCT No.: PCT/CN03/00188

§ 371 (c)(1),
(2), (4) Date: Mar. 29, 2005

(87) PCT Pub. No.: WO03/078469

PCT Pub. Date: Sep. 25, 2003

(65) Prior Publication Data

US 2005/0176933 A1 Aug. 11, 2005

(30) Foreign Application Priority Data

Mar. 15, 2002 (CN) ................ 02 1 14471

(51) Int. Cl.
*C07H 21/04* (2006.01)
*C12N 15/00* (2006.01)
*C12P 21/08* (2006.01)
*C07K 16/00* (2006.01)

(52) U.S. Cl. ............... 536/23.53; 435/320.1; 530/387.1; 530/387.3; 530/388.1

(58) Field of Classification Search ........................ None
See application file for complete search history.

(56) References Cited

U.S. PATENT DOCUMENTS 5,618,920 A * 4/1997 Robinson et al. ......... 530/387.1

6,335,163 B1 * 1/2002 Sharon .......................... 435/6

OTHER PUBLICATIONS

Colman. Research in Immunology, 145:33-36, 1994.*
Paul, Fundamental Immunology, 3rd Edition, 1993, pp. 292-295.*
Rudikoff et al. Proc. Natl. Acad. Sci. USA, 79:1979-1983, Mar. 1982.*
Yang et al. World J. Gastroentero., 2001. 7:216-221.*
Mac Callum, Martin, and Thornton. Antibody-antigen interactions: contact analysis and binding site topography. Journal of Molecular Biology, 1996. vol. 262, pp. 732-745.*
Pascalis, Iwahashi, Tamura, Padlan, Gonzales, Santos, Giuliano, Schuck, Schlom, and Kashmiri. Journal of Immunology, 2002. vol. 169, pp. 3076-3084.*
Cassett, Roux, Mouchet, Bes, Chardes, Granier, Mani, Pugniere, Laune, Pau, Kaczorek, Lahana, and Rees. Biochemical and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, McKay, De Vos, and Lowman. Selection and analysis of an optimized anti-VEGF antibody: crystal structure of an affinity-matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*

* cited by examiner

*Primary Examiner*—David J. Blanchard
*Assistant Examiner*—Anne M. Gussow
(74) *Attorney, Agent, or Firm*—Davidson, Davidson & Kappel, LLC

(57) ABSTRACT

The present invention relates to the anti-human hepatocarcinoma McAb HAb18 heavy chain and light chain variable region genes, the polypeptides encoded by the same, as well as to their use in the preparation of a medicament for diagnosing and treating tumors or inflammation diseases. Based on the heavy chain and light chain variable region genes, various novel small molecule genetic engineering antibodies, including single chain antibodies, chimeric antibodies, Fab antibodies and the like can be constructed and expressed for the diagnosis and treatment of hepatoma.

8 Claims, 6 Drawing Sheets

FIG. 3  Construction of the Fab gene expression vector.
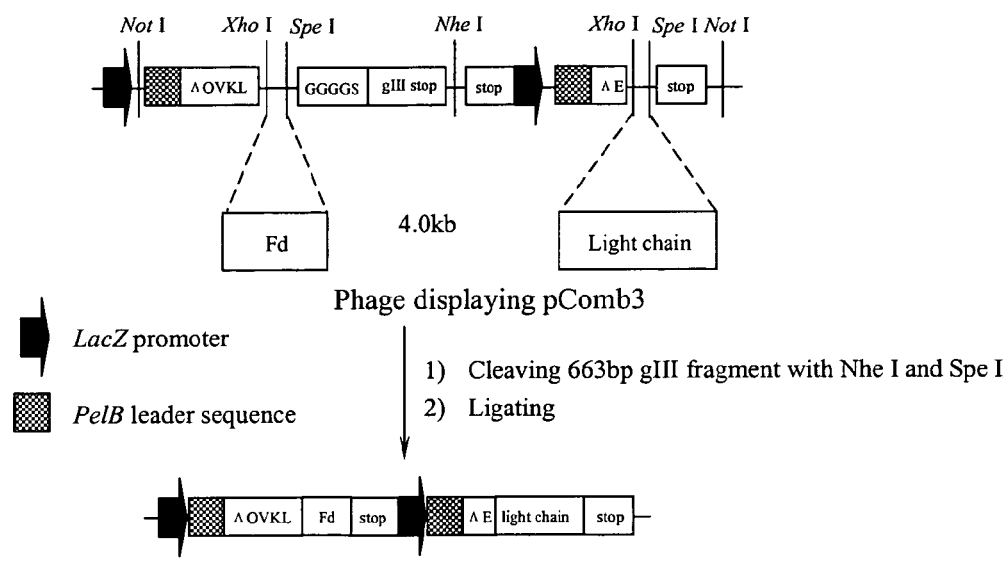
FIG. 4
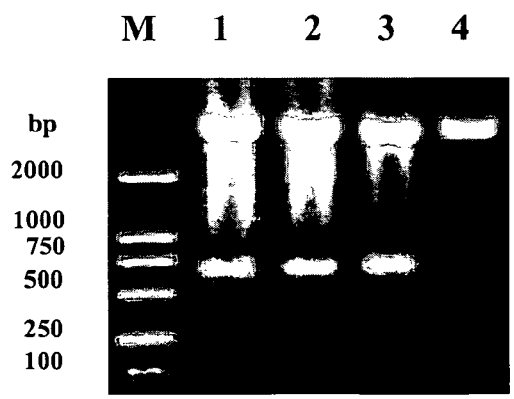

FIG. 5  Detection of the binding activities of Fab and HAb18 by competitive ELISA
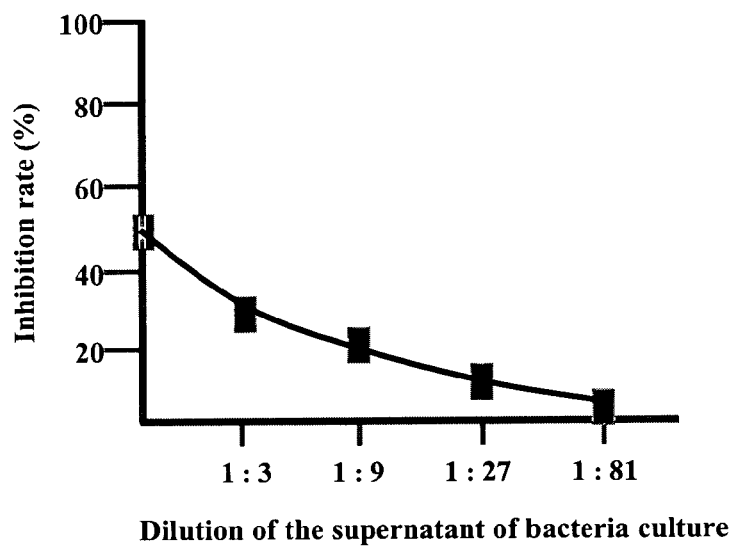
FIG. 6
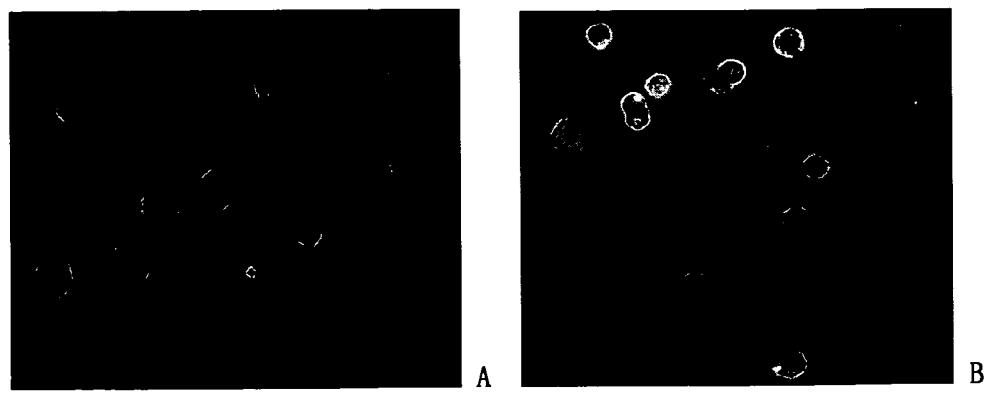

FIG. 7
FIG. 8 Construction of the chimeric Fab gene (cFab) expression vector
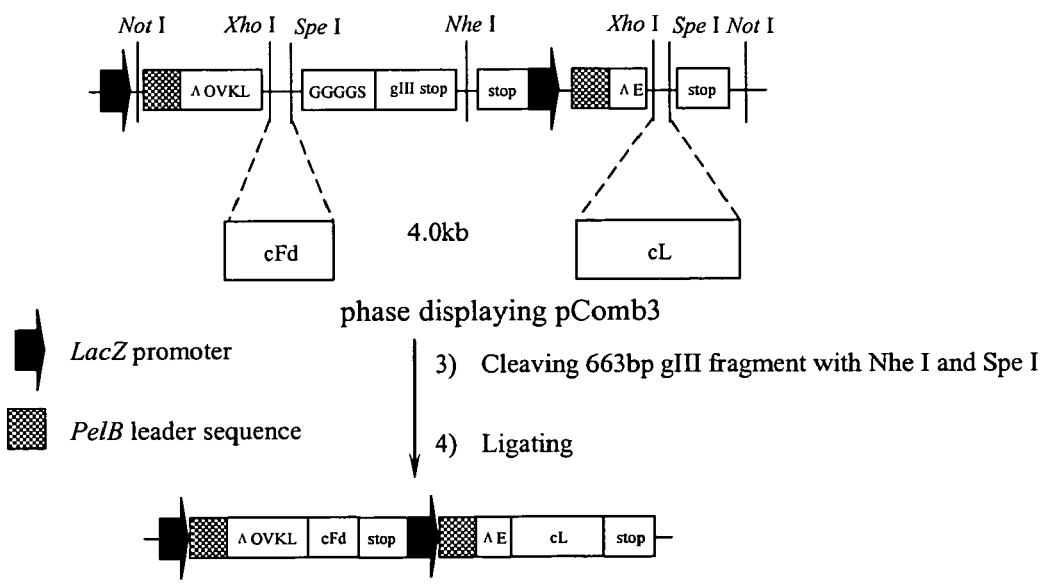

FIG. 9
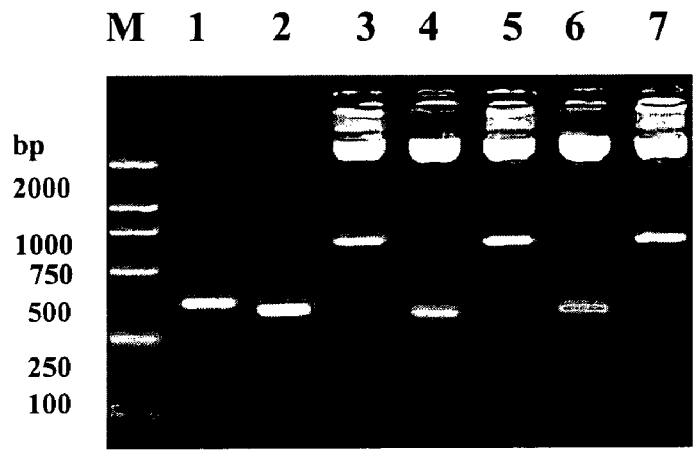
FIG. 10 ELISA detection result of the binding activity of cFab.
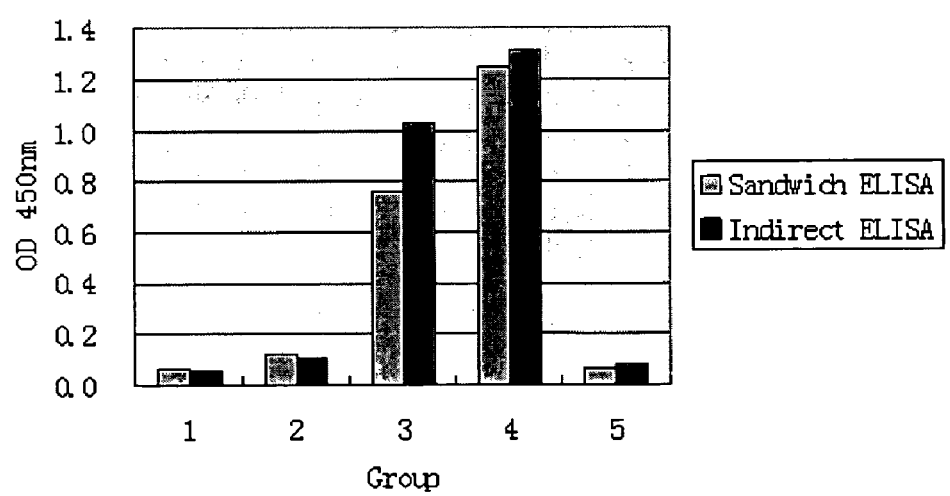

FIG. 11 Detection of the binding activities of cFab with HAb18 by competitive ELISA
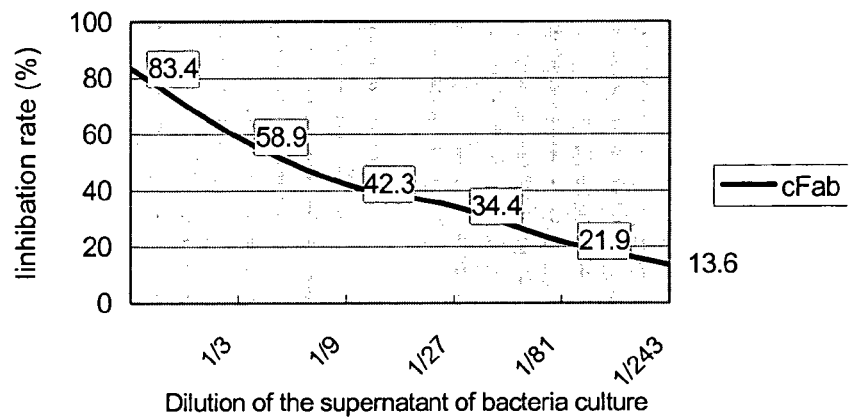
FIG. 12
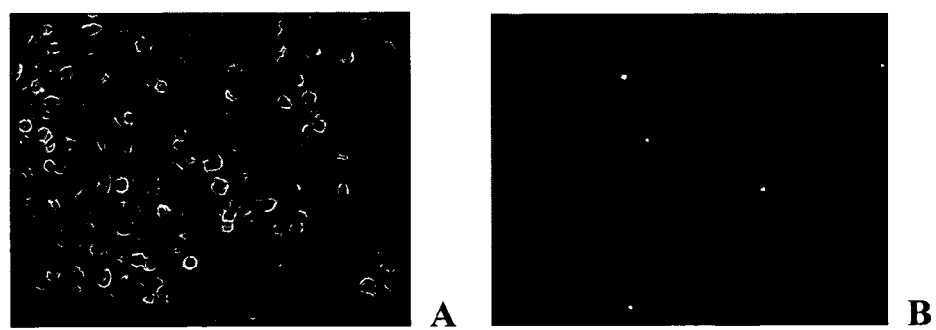

VARIABLE REGION GENE OF HEAVY/LIGHT CHAIN OF ANTI-HUMAN HEPATOMA MONOCLONAL ANTIBODY HAB 18 AND USE THEREOF

This application is a National Phase 371 application of International Patent Application Ser. No. PCT/CN03/00188, filed Mar. 17, 2003, which claims priority from Chinese Patent Application No. 02114471.0, filed Mar. 15, 2002.

FIELD OF THE INVENTION

This invention relates to the anti-human hepatoma monoclonal antibody (McAb) HAb18 heavy/light chain variable region genes and the coded polypeptides thereof, and to the use of the genes and polypeptides in the preparation of medicaments for diagnosing and treating tumors or inflammatory diseases.

BACKGROUND OF THE INVENTION

Hepatoma is a common disease with high morbidity in China and Southeast Asia. Particularly in China, about 110,000 patients die of hepatoma each year, which holds 43% among the total dead hepatoma patients in the world. Therefore, it still requires comprehensive and profound research on hepatoma diagnosis and therapy. A variety of McAbs have been identified since hybridoma technology was established by Kohler and Milstein in 1975. These McAbs shed new light on the preclinical and clinical research and anti-hepatoma McAbs are no exception. In the past 20 years, traditional production of anti-hepatoma antibodies has focused on such target molecules as α-fetoprotein and ferritin. In these processes, traditional immunization methods are adopted, i.e. with the soluble extraction materials of hepatocarcinoma or cultured hepatocarcinoma cells as the immunogen. However, it is difficult to generate anti-hepatoma antibodies with high affinity and specificity by these methods because of the variation, instability or partial loss of the tumor antigenic epitopes.

There are several successful reports on antibody generation using cell suspensions derived from fresh tumor tissue to immunize animals. In spite of the complicated screening, antigenicity can be better retained in this way. The inventors have successfully obtained seven clones of specific anti-hepatoma antibodies using this method. The detailed process for the establishment of these hybridoma cell strains that secret murine anti-hepatoma antibodies is shown in Zhinan Chen, Yanfang Liu, Jizheng Yang et al., *McAb Communications*, 1989; 2: 33-36. Among these antibodies, anti-human hepatoma McAb HAb18 was found to have higher specificity, with an immunohistochemistry positive rate up to 75%. Starting from anti-human hepatoma McAb HAb18, the inventors have successfully cloned heavy and light chain variable region genes. With the advances of the research of genetically engineered antibody, this invention establishes a solid basis to develop novel small molecule genetically engineered antibody.

SUMMARY OF THE INVENTION

In one aspect, the invention relates to the variable region genes of the monoclonal antibody HAb18 against hepatoma-associated antigen HAb18G. These McAb HAb18 variable region genes were cloned from a hybridoma cell line HAb18 that can secret murine anti-HAb18G monoclonal antibodies with high activity. The full length of the heavy chain variable region gene is 445 bp, with a nucleic acid sequence shown in SEQ ID NO: 1. The amino acid sequence encoded by this gene is shown in SEQ ID NO: 3. The full length of the light chain variable region gene is 421 bp, with a nucleic acid shown in SEQ ID NO: 2. The amino acid sequence encoded by this gene is set forth in SEQ ID NO: 4. After recombination, these two genes may be used to express active antibody fragments which can specifically identify and bind the hepatoma-associated antigen HAb18G. It is contemplated that the invention also comprises those sequences that can hybridize with the sequences in SEQ ID NO: 1 or SEQ ID NO: 2 under stringent hybridization conditions, for example, the conditions stated in *Molecular Cloning* (Cold Spring Harbor Laboratory).

In another aspect, the invention relates to a Fab gene comprising the heavy chain and the light chain variable region genes, a murine-human chimeric Fab gene, as well as the gene products thereof, namely a Fab antibody and chimeric Fab antibody.

In still another aspect, the invention relates to the use of the genes and polypeptides of the invention in the preparation of medicaments for diagnosing and treating tumors or inflammation diseases.

DETAILED DESCRIPTION OF THE INVENTION

Using a set of designed primers, the inventors have cloned the McAb HAb18 heavy chain and light chain variable region genes from a hybridoma cell line HAb18 that can secret specific monoclonal antibodies against hepatoma. Sequence analysis shows that the heavy chain variable region gene (VH gene) is highly homologous with the variable region gene of the autoantibody against thymocytes and erythrocytes described by Kasturi, K. N et al. The light chain variable region gene (VL gene) belongs to the V-J region gene of the rearranged κ chain of mouse immunoglobulin, and has highest homology with the anti-DNA antibody 6E6 light chain variable region gene, which was described by O'Connor, K. C et al. The VH and VL genes of the invention encode accurate variable regions of the mouse antibody. With these genes, a variety of novel small molecule antibodies, including single chain antibody, chimeric antibody, Fab antibody, and the like, may be constructed and expressed by genetic engineering for the diagnosis and therapy of hepatoma.

So far, monoclonal antibodies against hepatoma are mainly used in research on hepatocarcinoma associated antigens. The development of monoclonal antibodies provides an effective way to discover novel tumor associated antigens or new target sites. These antigens can be used in clinical serum tests and are helpful in diagnosing and evaluating therapeutic efficacy. Monoclonal antibodies can also be used in research on hepatoma monoclonal-antibody-targeted drugs. Radioimmunodiagnosis, targeted chemotherapy, and radiotherapy with McAbs as carriers have made substantial progress in recent years. In this regard, drugs such as chemical compound-McAb conjugates, cytotoxin-McAb conjugates and radionuclide-McAb conjugates have been developed.

The light and heavy chain variable region genes of the invention can be used to construct certain protein medicaments, which can be directly used in the diagnosis and treatment of relevant diseases, especially tumors and inflammation diseases. The polypeptide encoded by the genes of the invention can be conjugated with a cytotoxin, a toxin, a radionuclide, an enzyme or a biological response modifier, so as to be used as targeted drugs in the diagnosis and therapy of certain diseases, especially tumors.

From the polypeptides encoded by the genes of this invention, new types of antibodies such as chimeric antibodies, humanized antibodies, small molecule antibodies, multi-covalent miniantibodies, bispecific antibodies, recombinant antibody fusion proteins, recombinant immunotoxins and phage antibodies may be constructed.

For a chimeric antibody, the variable region of a mouse McAb may be linked with the constant region of a human Ig. Desirable efficacies in tumor therapy have been achieved by using such chimeric antibodies because these antibodies have reduced side effects such as the HAMA response while maintaining the specificity and affinity of a mouse McAb.

To obtain a humanized antibody, the structure of variable region genes is humanized by means of CDR graft, surface amino veneer, framework exchange, located reservation and epitope-directed selection. A humanized antibody can keep the specificity and affinity of a mouse McAb.

Small molecule antibodies include Fab antibodies consisting of VH-CH1 and VL-C1, single chain antibodies formed by linking VH and VL genes with a polypeptide linker (Gly4Ser)$_3$, Fv fragment antibodies formed by non-covalent linkage of VH and VL, single domain antibodies comprising only one domain of VH or VL, and minimal recognition units constructed by single CDR, and the like.

Multi-covalent miniantibodies mainly include double chain antibodies, (ScFv)$_2$, Flex mini-antibodies, LD miniantibodies, F(ab')$_2$, F(ab')$_3$, (ScFv)$_4$, etc. The multi-covalent miniantibodies have good potential value in clinical applications because they have multiple antigen binding sites, high affinity, moderate molecule size, high ability to penetrate tumor tissues, and slow clearance rate in kidney.

Bispecific antibodies, also called bifunctional antibodies, have double specificities and functions.

Recombinant antibody fusion proteins are recombinant proteins capable of targeting a specific biological activity at a target site, and are prepared by linking a Fab or Fv gene with a gene encoding a non-antibody protein such as a toxin or an enzyme.

Recombinant immunotoxins are produced by linking a gene for a toxin and a gene for an antibody and expressing the resultant gene. They have low non-specificity, are stable and safe in vivo and easily penetrate into tumors.

A phage antibody is obtained by linking an Ig V gene with a phage gene III or gene VIII, then the gene is transfected into host bacteria, which expresses the fusion protein of Fab or ScFv on the surface of a phage membrane. Through several affinity pannings, specific antibodies can be obtained.

Using the polypeptides encoded by the heavy chain and light chain variable region genes of the invention as a carrier, various anti-cancer or anti-inflammation agents may be conjugated with said polypeptides so as to form immunoconjugates or targeted drugs. For example, the immunoconjugates or targeted drugs can be in the form of a conjugate of an antibody and a nuclide. Such a conjugate is able to direct the nuclide efficiently to local tumor tissues, reducing the damage to normal tissues incurred by irradiation during radiotherapy. The conjugate also allows a targeted diagnosis and treatment of tumors, termed radioimmunoimaging and radioimmunotherapy respectively. Nuclides normally used to conjugate with a monoclonal antibody include $^{125}$I, $^{131}$I, $^{111}$In, $^{90}$Y, $^{99}$Tc$^m$, $^{188}$Re and $^{186}$Re, and the like.

The immunoconjugates or targeted drugs can also be in the form of a conjugate of an antibody and a chemotherapy drug. Such a conjugate directs the drug specifically to tumors, reducing the damage to normal tissues and the side effects caused by chemotherapy drugs. Chemotherapy drugs commonly used to conjugate with antibodies include alkylating agents such as phosphoramides, anti-metabolites such as methotrexate and 5-flurouracil, antibiotics such as adriblastine, epirubicin, cerubidin, leurocristine and mitomycin.

The immunoconjugates or targeted drugs can also be in a form of a conjugate of an antibody and a toxin, which is also called an immunotoxin. Immunotoxins have strong cytotoxicity and are independent from biological auxiliary mechanisms. Because immunotoxins have a mechanism different from traditional chemotherapy and radiotherapy for killing tumors, they can be used to treat tumors on which chemotherapy and radiotherapy have poor effects. Toxins that may be used to conjugate with an antibody include ricin, diphtheria toxin, ormosia toxin, soapwort, pseudomonas exotoxin, streptolysin, porforin, etc.

The immunoconjugates or targeted drugs can also be in the form of a conjugate of an antibody and a biological response modifier (BRM). Although BRMs alone can adjust the immune function of human body and kill tumor cells with good efficiency, its function is not exerted completely because only a part of the BRM injected can arrive at the target site. BRMs also have some side effects. If a BRM is conjugated with a McAb, the McAb can guide the BRM to the target site and kill tumor cells. BRM includes INF and IL-2.

The immunoconjugates or targeted drugs can also be in the form of an antibody-targeted prodrug. Antibodies are conjugated with an enzyme that can specifically activate prodrugs. The conjugate is first injected into the body, after some time, a prodrug is injected, which can be converted into an active drug at tumor site and kill tumor cells. At present, some compounds can be used as prodrugs, including glutamine derivatives of benzoic acid hydrogen mustard, phosphoric acid podophyllum ethylidene, phosphoric acid mitocin-C, glycoside cerubidin, adriblastine, 5-fluorocytosine and cephalothin chlorethazine. The activating enzymes include carboxypeptidase G$_2$, alkaline phosphatase, penicillin amidase, β-lactamase, cytosine deaminase, β-glycosidase, and aminopeptidase.

The immunoconjugates or targeted drugs can also be in the form of an immune liposome, in which a McAb is conjugated to the surface of a liposome. Because the liposome can encapsulate large amounts of drugs and the antibody can bind antigen specifically, immune liposomes with encapsulated drugs have improved specificity and efficacy.

DESCRIPTION OF THE FIGURES AND PREFERRED EMBODIMENTS

The invention is further described with reference to the following figures and examples.

BRIEF DESCRIPTION OF THE DRAWINGS

FIG. 3. Construction diagram of the Fab expression vector.

FIG. 4. Restriction analysis of recombinant expression vector pComb3/Fd-L. 1, pComb3/Fd-L/Xho I+Spe I; 2, pComb3/Fd-L/Sac I+Xba I; 3, pComb3/Fd-gIII-L/Spe I+Nhe I; 4, pComb3/Fd-L/Spe I+Nhe I.

FIG. 5. Competitive ELISA assay for the binding activities of Fab and HAb18 with corresponding antigen.

FIG. 6. Immuno-fluorescence detection of the reactivity of McAb HAb18 and Fab fragments thereof with Hepatocarcinoma cell line HHCC. A, Immuno-fluorescence staining using HAb18 Fab; B, Immuno-fluorescence staining using HAb18.

FIG. 7. Restriction analysis of the recombinant expression vector pComb3C. M, DNA marker; 1, human IgG3CH1; 2, human κ chain constant region; 3, pComb3C/XhoI+Spe I; 4, pComb3C/Sac I+Xba I; 5, pComb3C/EcoR V+Sal I.

FIG. 8. Construction of the expression vector containing the chimeric Fab gene (cFab).

FIG. 9. Restriction analysis of recombinant cFab expression vector pComb3C/cFab. M, DNA marker; 1, VH; 2, VL; 3, pComb3C/cFab-gIII/Xho I+Spe I; 4, pComb3C/cFab-gIII/EcoRV+Spe I; 5, pComb3C/cFab-gIII/Sac I+Xba I; 6, pComb3C/cFab-gIII/Sal I+Xba I; 7, pComb3C/cFab-gIII/Spe I+Nhe I.

FIG. 10. ELISA assay for the binding activity of cFab. 1, supernatant of lysed bacteria transformed with empty vector; 2, supernatant of lysed bacteria transformed with pComb3, before induction; 3, bacteria transformed with pComb3C/cFab, after induction; 4, chimeric HAb18IgG; 5, PBS.

FIG. 11. Competitive ELISA detection of the binding activities of cFab and HAb18 with corresponding antigen.

FIG. 12. Immuno-fluorescence detection of the reactivity of the chimeric HAb18IgG and its cFab with Hepatocarcinoma cell line HHCC. A, Staining with HAb18 cFab; B, Staining with chimeric HAb18IgG.

EXAMPLES

Example 1

Cloning of the Genes Encoding the Variable Regions of Heavy/Light Chain of Anti-Human Hepatoma McAb HAb18

The cell line used was a murine hybridoma cell line obtained by using a conventional cell fusion technique by the Cell Engineering Researching Center of the Fourth Military Medical University (FMMU) (Zhinan Chen, Yanfang Liu, Jizheng Yang et al. McAb communication. 1989; 2:33-36). The antibody produced by the cell line was a murine anti-human hepatoma McAb HAb18, which was an IgG, with high affinity and specificity to its target molecule HAb18G.

Figure 1:
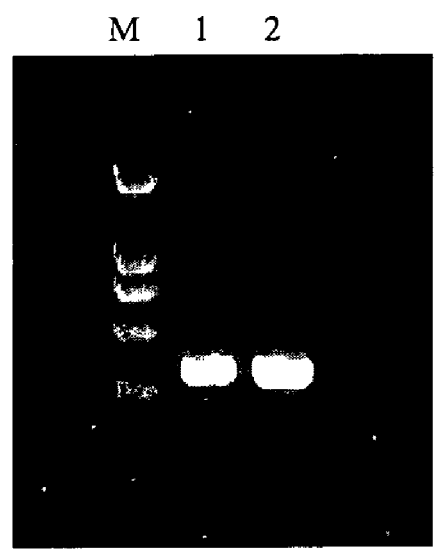
FIG. 1. Agarose gel electrophoresis of the heavy/light chain variable region genes of anti-human hepatoma McAb HAb18 amplified by RT-PCR. A, DL-2000 marker; B, heavy chain variable region gene of McAb HAb18; C, light chain variable region gene of McAb HAb18.

Cells ($5 \times 10^6$) in exponential growth phase were used to prepare total RNA. Typically, total RNA extraction was carried out using an SV Total RNA Isolation System according to the protocol provided by the manufacturer (Promega, USA). The quality and quantity of the sample were determined by ultraviolet spectroscopy and 1% denaturing polyacrylamide gel electrophoresis. A first strand cDNA corresponding to the variable region of the antibody was obtained by reverse transcription using random primers Oligo(dT)$_{15}$ (Promega, USA). The genes encoding the variable regions of heavy chain and light chain (VH and VL) of murine anti-human hepatoma McAb HAb18 were amplified by PCR with a set of universal primers. The PCR products VH (about 450 bp) and VL (about 421 bp) were separated on a 1.5% agarose gel and isolated by cutting the gel, recovered and purified by using a gel purification kit (Promega Inc), and then identified by agarose gel electrophoresis (FIG. 1). The fragments of interest were cloned respectively into vector pMD-18-T and then subjected to sequence analysis.

Oligo(dT)$_{15}$ (Promega, USA) was used as a random primer for reverse transcription. The volume of the reaction system was 20 μL, containing 1 μg of total RNA (2 μL), 0.5 μg random primers Oligo(dT)$_{15}$ (1 μL), 4 μL MgCl$_2$ (25 mM), 2 μL 5×dNTPs, 2 μL 10× Buffer, 0.5 μL RNase inhibitor. The reverse transcription was carried out in the presence of 0.75 μL of AMV reverse transcriptase enzyme (15U). RNase-free water was added to reach a total volume of 20 μL. The mixture was incubated at 42° C. for 60 min and then boiled for 3 min. The product obtained was then kept at −20° C. until use.

For PCR amplification of VH and VL genes, reactions were carried out in a final reaction volume of 50 μL which contained 5 μL first strand cDNA, 30 pmol (5 μL) of reverse and forward primers (the primers are described below), 0.4 mM each of dNTPs, 5 μL 10× buffer and 1.25U Ex Taq DNA polymerase. Water was added to reach a final volume of 50 μL, mixed and a drop of paraffin oil was then added into the mixture. After heated for 3 min at 94° C., amplification was performed for 35 cycles with 94° C. 1 min, 54° C. 1 min, and 72° C. 1 min for each cycle, and finally the extension reaction was at 72° C. for 10 min.

Cloning of desired fragment into a T vector was conducted as follows. PCR products were recovered on an agarose gel and cloned into pMD18-T. The ligation reaction contained 1 μL of vector pMD18-T, 3 μL of purified PCR product (VH or VL gene), 1 μL de-ionized H$_2$O and 5 μL of ligation buffer. The reaction system was incubated at 4° C. overnight. The product was transformed into *Escherichia coli* JM109. Recombinant clones were selected and then sequenced using universal primers.

The designed primers used for the amplification of the genes of variable regions of heavy and light chains of McAb HAb18 were as follows (underlined portions represent restriction sites):

5' Primers for the Variable Region of the Heavy Chain of the Mouse Antibody:

(1) 5'-GG<u>GATATC</u>CACCATGG(AG)ATG(CG)AGCTG(TG)GT(CA)AT(CG)CTCTT-3'  (SEQ ID NO:5)

(2) 5'-GGG<u>GATATC</u>CACCATG(AG)ACTTCGGG(TC)TGAGCT(TG)GGTTTT-3'  (SEQ ID NO:6)

(3) 5'-GGG<u>GATATC</u>CACCATGGCTGTCTTGGGGCTGCTCTTCT-3'  (SEQ ID NO:7)

3' Primer for the Variable Region of the Heavy Chain of the Mouse Antibody:

5'GAC(ACT)CATGGGG(CG)TGT(TC)GT<u>GCTAGC</u>TG(AC)(AG)GAGAC(AGT)G  (SEQ ID NO:8)
TGA-3'

5' Primers for the Variable Region of the Light Chain of the Mouse Antibody:

(1) 5'-GGG<u>GATATC</u>CACCATGGAGACAGACACACTCCTGCTAT-3'  (SEQ ID NO:9)

(2) 5'-GGG<u>GATATC</u>CACCATGGATTTTCAAGTGCAGATTTTCAG-3'  (SEQ ID NO:10)

(3) 5'-GGG<u>GATATC</u>CACCATGGAG(AT)CACA(GT)(AT)CTCGGGTCTTT(GA)TA-3'  (SEQ ID NO:11)

(4) 5'-G<u>GATATC</u>CACCATG(GT)GCCC(AT)(AG)CTCAG(CT)TC(CT)CT(TG)GT-3'  (SEQ ID NO:12)

(5) 5'-GGG<u>GATATC</u>CACCATGAAGTTGCCTGTTAGGCTGTTG-3'  (SEQ ID NO:13)

3' Primer for the Variable Region of the Light Chain of the Mouse Antibody:

5'-GGATACAGTTGGTGGTGCA<u>GTCGAC</u>TTACGTTT(GT)GTTTCA(AG)CTT-3'  (SEQ ID NO:14)

The sequences of the genes encoding the variable regions of heavy/light chain (VH and VL) were referred to as SEQ ID NO:1 and SEQ ID NO:2, and their amino acids sequence were referred to as SEQ ID NO:3 and SEQ ID NO:4, respectively.

Example 2

Cloning and Expression of the Gene Encoding Fab of Anti-Human Hepatoma McAb HAb18

The relative molecular weight of Fab is about 50,000. The Fab fragment has good penetration and pharmacokinetics properties and has been widely used in the diagnosis and therapy of many diseases. In this example, the gene encoding the Fab fragment of McAb HAb18 was cloned and expressed in E. coli.

1. Materials and Methods 1.1 Materials

A murine hybridoma cell line producing a murine anti-human hepatoma McAb HAb18 (IgG$_1$) was obtained by using a conventional cell fusion technique (Zhinan Chen, Yanfang Liu, Jizheng Yang et al. McAb communications. 1989; 2:33-36). Trizol reagent (Gibco BRL) and a Reverse Transcription kit (Promega, USA) were used. Expression vector pComb3 and E. coli competent cell JM109 and XL1-blue were commercially obtained. T vector, PCR reagents, restriction endonucleases and ligase were purchased from Takara (Dalian, China). McAb HAb18 and HRP-HAb18 were made by the inventors (Zhinan Chen, Yanfang Liu, Jizheng Yang et al. McAb communications. 1989; 2:33-36). IPTG-, FITC- and HRP-labeled goat anti-mouse IgGs were purchased form SABC Co. A hepatocarcinoma cell line HHCC was maintained and cultured by the Cell Engineering Researching Center of the FMMU. Primers for PCR were synthesized by Sai Bai Sheng Biotech Company (Beijing, China), with the following sequences: Fd 5'primer: 5'-AAG TGA AGC TT<u>CTCGAG</u> CTGG-3' (SEQ ID NO: 15), Fd 3'primer: 5'-AGG CTT <u>ACTAGT</u> ACA ATC CCT GGG CAC AAT-3' (SEQ ID NO: 16). Light Chain 5'primer: 5'-GAT GT <u>GAGCTCG</u> TGA TGA CCC AGA CTC C-3' (SEQ ID NO: 17), Light Chain 3' primer: 5'-GCG CCG CCG <u>TCTAGA</u> ATT AAC ACT CAT TCC TGT TGA A-3' (SEQ ID NO: 18). The underlined sequences respectively represent the restriction sites of Xho I, Spe I, Sac I, and Xba I.

1.2 Methods 1.2.1 Cloning of the Fab Genes of HAb18 McAb:

The total RNA was extracted from the hybridoma cell secreting McAb Hab 18 using Trizol reagent and reverse transcribed into cDNA. The cDNA was used as a template to amplify the Fd and light chain genes. The PCR products were purified by agarose gel and separately cloned into pMD18-T to construct pMD18-T/Fd and pMD18-T/L vectors. After the vectors were transformed into Escherichia coli JM109, positive clones were screened and then sequenced.

1.2.2 Construction of the HAb18 Fab Expression Vector

The expression vector pComb3 and the cloning vector pMD18-T/L were digested with restriction endonucleases Sac I and Xba I. Positive clones were selected after ligation of gel-purified digested fragments and transformation, and confirmed by restriction analysis. The obtained light chain expression vector pComb3/L and the cloning vector pMD18-T/Fd were respectively digested with restriction endonucleases XhoI and Spe I. Fab display expression vector pComb3/Fd-gIII-L was obtained after ligation of gel-purified digested fragments, transformation, selection and confirmation. Finally, the vector pComb3/Fd-gIII-L was cut by restriction endonuclease enzymes SpeI and NheI to remove gIII gene fragment and then circularized by T4 DNA ligase to generate a new secretory expression vector pComb3/Fab-L. The desirable clone was obtained after transformation, screening and restriction analysis.

1.2.3 Expression of the Fab Gene

Single colonies of correct recombinant clones were inoculated separately in 2 mL SB-A medium containing 100 mg/L ampicillin and grown overnight at 37° C. The second day, after transfer the culture into SB-A medium in a ratio of 1:100, the culture was maintained at 37° C. until $A_{600}$ was between 0.4-0.6. Then IPTG was added to a final concentration of 1 mmol/L. The culture was then maintained at 30° C. overnight. After centrifugation, the bacteria cells were harvested. Then they were freezed and thawed time and again. The supernatant was harvested after centrifugation for further test.

1.2.4. Sandwich ELISA Detection of the Expression of Fab

An ELISA plate was coated with goat anti-mouse IgG (10 mg/L) and then incubated overnight at 4° C., defatted milk (50 g/L) was used to block all the wells to prevent non-specific binding. After blocking for 1 hour, the supernatants of untransformed bacteria, the non-induced pComb3/Fd-L transformant, and the induced pComb3/Fd-L transformant were added. McAb HAb18 was used as positive control and PBS as blank control. Finally, goat anti-mouse IgG-HRP was added with TMB as a substrate to develop color.

1.2.5 Detection of the Antigen Binding Activity of the Expression Product

1) Indirect ELISA

The wells of a microtiter plate were coated with purified GST and a prokaryotic expression product GST-HAb18GE (a fusion of the extracellular domain of hepatoma-associated antigen HAb18G with GST). Supernatants of untransformed bacteria, non-induced transformant, and induced transformant were detected. McAb HAb18 was used as positive control and PBS as blank control.

2) Competitive ELISA

The wells of microtiter plate were coated with purified GST-HAb18GE at 4° C. overnight, and the wells were blocked with 50 g/L defatted milk. Then a mixture of equal amounts of HRP-HAb18 (0.1 mg/L) and different dilutions of the supernatant of the induced transformant were added. After incubation and washing, TMB was used to develop color. $A_{450}$ was measured and the inhibition rate was calculated. % Inhibition=[($A_{450}$ of control group–$A_{450}$ of inhibition group)/$A_{450}$ of control group]×100%.

3) Immuno-Fluorescence Staining

A cell suspension of HHCC which highly expressed antigen HAb18G was prepared. The concentration of the HHCC suspension was adjusted to $5\times10^9$-$1\times10^{10}$ cells/mL. HAb18 Fab was diluted with horse blood serum and then added to the HHCC suspension and incubated for 30 minutes at 4° C. Cells were washed twice, FITC conjugated rabbit anti-mouse IgG was then added and incubated at 4° C. for 30 minutes. After washing twice, cells were fixed and mounted and then observed under a fluorescent microscope. In this experiment, McAb HAb18 was used as a positive control, PBS as blank control, and an anti-encephalitis virus McAb as a negative control.

Figure 2:
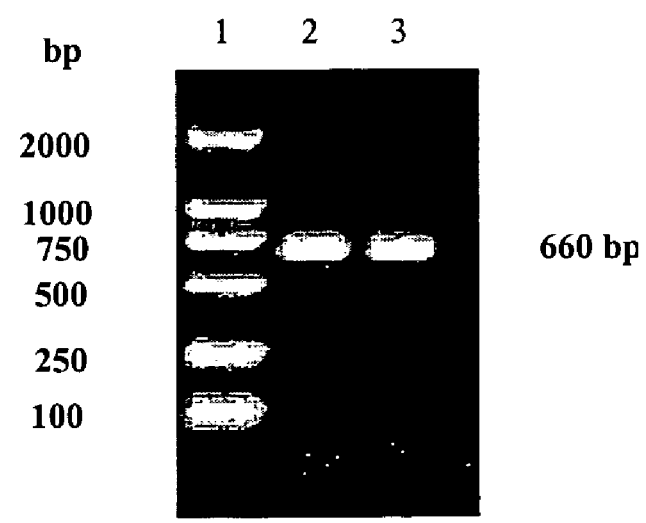
FIG. 2. Agarose gel electrophoresis analysis of the PCR-amplified product of the gene for a Fab of anti-human hepatoma McAb HAb18. 1, DL-2000 Marker, 2, Fd gene, 3, light chain gene.

2 Results 2.1 Amplification of Fab Gene and Construction of the Expression Vector The genes encoding Fd and light chain of McAb HAb18 were amplified by RT-PCR using Fd 5' and 3' primers for Fd and 5' and 3' primers for light chain, respectively. The amplified products were separated by 10 g/L agarose gel. As expected, both products were 660 bp in length (FIG. 2). Then, the genes encoding Fd and light chain of McAb HAb18 were cloned into pMD-18-T and sequenced. Sequence analysis showed that the sequences of the genes encoding variable regions of heavy chain and light chain (VH and VL) were identical to those of the variable region genes of HAb18 cloned in Example 1. $C_{H1}$ belonged to IgG1 and $C_L$ belonged to κ. The construction of the recombination vector pComb3/Fd-L is shown in FIG. 3. Restriction analysis showed that the gene fragments of interest (about 660 bp) had been inserted into the vector pComb3 in one copy (FIG. 4).

2.2 Expression and Identification of Fab

Sandwich ELISA detection showed that Fab was expressed by the recombination vector pComb3/Fd-L after IPTG induction (Table 1). Results from indirect ELISA also showed that the expressed Fab was capable of specifically binding with the extracellular domain of hepatoma-associated antigen HAb18G (Table 1). The competitive ELISA further showed that the expressed Fab could competitively inhibit the binding of HAb18 with its specific antigen. The inhibition rate decreased with the decrease of the concentration of the expressed product (FIG. 5). The immuno-fluorescence staining revealed that the expressed Fab could specifically bind with hepatocarcinoma cell line HHCC (FIG. 6A), but with a fluorescent intensity weaker than that of the positive control (FIG. 6B). No immuno-fluorescence staining was observed in negative control (not shown).

TABLE 1

ELISA analysis of the Fab binding activity ($\chi \pm S$)

| Groups | Results of Sandwich ELISA($A_{450}$) | Results of Indirect ELISA($A_{450}$) |
|---|---|---|
| Transformant with empty vector* | 0.075 ± 0.004 | 0.075 ± 0.004 |
| Transformant with pComb3/Fd-L, not induced* | 0.017 ± 0.002 | 0.098 ± 0.008 |
| Transformant with pComb3/Fd-L, induced | 0.633 ± 0.014$^a$ | 0.379 ± 0.013$^a$ |
| HAb18 | 1.271 ± 0.016 | 1.018 ± 0.012 |
| PBS | 0.059 ± 0.03 | 0.068 ± 0.002 |

$^a$p < 0.01, compared with transformant with empty vector;
*the supernatant of the transformant culture.

Example 3

Construction of a Universal Expression Vector for a Chimeric Human/mouse Fab Antibody and Expression of the Chimeric Fab Antibody Against Human Hepatoma Associated Antigen HAb18G HAb18 McAb is a murine monoclonal antibody with high specificity and affinity for human hepatoma associated antigen HAb18G/CD147. A murine antibody can elicit human anti-mouse antibody (HAMA) reaction to different extents in the body of patients. This reaction will weaken the therapeutic efficacy of the antibody, produce toxicity and damage the organs for elimination. In addition, owing to its poor penetrating ability, the clearance of a large antibody molecule in blood and non-tumor tissues is relatively slower, leading to the lower T/NT ratio, which limits the further application of said antibody. In order to overcome these defects, it is necessary to develop a new type of genetically engineered antibody with low immunogenicity and high T/NT ratio. The relative molecular weight (Mr) of chimeric Fab is about 50,000, making it have better penetration and pharmacokinetic characteristics. Fabs have been used in diagnosing and treating various diseases. In this example, starting from the Fab antibody constructed according to Example 2, a partially humanized Fab antibody was constructed by replacing the murine mCH1/mCL with huCH1/huCL in order to decrease the HAMA response to a great extent.

1. Materials and Methods 1.1 Materials

The vector pComb3/HuFab containing human IgG3CH1 and κ light chain constant region genes was kindly provided by Dr Wen, Department of Biochemistry, FMMU, China. T vectors pMD18T-Fd and pMD18T-L containing, respectively, McAb HAb18 (IgG1) Fd and the entire light chain were constructed by the inventors. Expression vector pComb3 and E. coli competent cells JM109 and XLI-blue were purchased. T vector, PCR reagents, restriction endonucleases and ligase were purchased from Takara (Dalian, China). McAb HAb18, chimeric HAb18IgG and HRP-HAb18 were made by the inventors (Zhinan Chen, Yanfang Liu, Jizheng Yang et al. McAb communications. 1989; 2:33-36). IPTG-, FITC- and HRP-labeled goat anti-mouse IgGs were purchased form SABC Co. Hepatocarcinoma cell line HHCC was maintained and cultured by the Cell Engineering Researching Center of the FMMU. Primers for PCR were synthesized by SBC (Beijing, China), with the following sequences:

| | | |
|---|---|---|
| MVHback | 5'-AAG TGA AGC TTC TCG AGT CTG G-3' | (SEQ ID NO:19) |
| MVHfor | 5'-GGG GAT ATC TGC AGA GAC AGT GAG -3' | (SEQ ID NO:20) |
| HuCH1back | 5'-GGG GCT CGA GTT GAT ATC TCC ACC AAG GGC CCA TCG GTC-3' | (SEQ ID NO:21) |
| HuCH1for | 5'-GCA TGT ACT AGT TTT GTC ACA AGA TTT GGG -3' | (SEQ ID NO:22) |
| MVLback | 5'-CAGATGTGAGCTCAGTATTGTGATGACCCAGACTCC-3' | (SEQ ID NO:23) |
| MVLfor | 5'-GGG GTC GAC GTT TTA TTT CCA ACT TTG T-3' | (SEQ ID NO:24) |
| HuCLback | 5'-GTT CCG AGC TCA AGT CGA CCT GTG GCT GCA CCA TCT GTC-3' | (SEQ ID NO:25) |
| HuCLfor | 5'-GCG CCG TCT AGA ATT AAC ACT CTC CCC TGT TGA AGC TCT TTG TGA CGG GCG AAC TCA GGC CC-3' | (SEQ ID NO:26) |

The underlined sequences in the primers are the restriction sites of Xho I, EcoR V, Xho I, EcoR V, Spe I, Sac I, Sal I, Sac I, Sal I and Xba I, respectively.

1.2 Methods 1.2.1 Construction of the Universal Expression Vector for Chimeric Human/Mouse Fab Antibodies The vector pComb3/HuFab was used as template to amplify the human IgG3CH1 and κ light chain constant region genes. Primer pairs HuCH1back and HuCH1for, and HuCLback and HuCLfor were used respectively. The PCR reaction products were purified and retrieved using a gel purification kit, followed by ligating into the vector pMD18-T to construct cloning vectors pMD18-T/HuCH1 and pMD18-T/HuCκ. After the vectors were transformed to *Escherichia coli* JM109, positive clones screened by restriction analysis were sequenced. The expression vector pComb3 and the cloning vector pMD18-T/Hu C☐ were cleaved by restriction endonucleases SacI and XbaI. The desired fragments were separated by agarose gel electrophoresis. The pComb3/HuC☐ positive clones generated by ligation and transformation were selected and identified by restriction. Then, the vector pComb3/HuC☐ and cloning vector pMD18-T/HuCH1 were cleaved by XhoI+SpeI and desired fragments were ligated. After ligation, transformation, selection, and identification, a chimeric Fab displaying universal vector pComb3C was constructed.

1.2.2. The Construction of the Hab 18cFab Expression Vector

The heavy chain and light chain variable region genes VH and VL of McAb HAb18 were amplified using the vectors pMD18T-Fd and pMD18T-L as templates, respectively, with the corresponding primer pair of MVHback and MVHfor, or MVLback and MVLfor. The corresponding restriction sites were also incorporated simultaneously. Furthermore, SacI+SalI were used to cleave respectively the expression vector pComb3C and the PCR product that was amplified from the heavy chain variable region gene of mAb HAb18 when the gene was purified and retrieved by Gel Purification Kit. Through such genetic manipulations as purification of desired fragments by agarose gel electrophoresis, ligation, transformation, the pComb3 C/cL positive clones were selected and identified by restriction. Then, the constructed pComb3 C/cL and PCR product that was amplified from the light chain variable region gene of mAb HAb18 when the gene was purified and retrieved by Gel Purification Kit were cleaved by XhoI+EcoRV. After ligation, transformation, selection and identification procedures, the chimeric Fab displaying vector pComb3C/cFab-gIII was constructed. The gIII fragment in the correct recombinant pComb3C/cFab-gIII was cleaved by SpeI+NheI, which then circularized to a secretory expression vector pComb3C/Fab by T4 DNA ligase. Repeating the above transformation, selection and identification by restriction, the desired clones were obtained.

1.2.3 The Expression of the cFab Gene

An individual colony containing the correct identified recombinant clone was seeded in 2 mL of SB-A medium supplemented with 100 mg/L of ampicillin and cultured overnight at 37☐. On the next day, the culture was seeded in fresh SB-A medium at 1:100 and cultured at 37☐ until $A_{600}$ reached about 0.4-0.6. Then, IPTG was added in a final concentration of 1 mmol/L and cells were cultured overnight at 37° C. After centrifugation, the bacteria cells were harvested. Then they were freezed and thawed time and again. The supernatant was harvested after centrifugation for further test.

1.2.4. Sandwich ELISA Detection of the Expression of cFab

An ELISA plate was coated with goat anti-human IgG (10 mg/L) and then incubated overnight at 4° C., defatted milk (50 g/L) was used to block all the wells to prevent nonspecific binding. After blocking for 1 hour, the above-mentioned supernatants of untransformed bacteria, the non-induced pComb3/cFab transformant, and the induced pComb3/cFab transformant were added. HAb18IgG was used as positive control and PBS as blank control. Finally, goat anti-human IgG-HRP was added with TMB as a substrate to develop color.

1.2.5 Detection of the Antigen Binding Activity of the Expression Product

1) Indirect ELISA

The wells of a microtiter plate were coated with purified GST and a prokaryotic expression product GST-HAb18GE (a fusion of the extracellular domain of hepatoma-associated antigen HAb18G with GST). Supernatants of untransformed bacteria, non-induced transformant, and induced transformant were analyzed. HAb18IgG was used as positive control and PBS as blank control.

2) Competitive ELISA

The wells of a microtiter plate were coated with purified GST-HAb18GE at 4° C. overnight, and the wells were blocked with 50 g/L nonfat dried milk. Then a mixture of equal amounts of HRP-HAb18 (0.1 mg/L) and different dilutions of the supernatant of the induced transformant were added. After incubation and washing, TMB was used to develop color. $A_{450}$ was measured and the inhibition ratio was calculated. % Inhibition=$[(A_{450}$ of control group$-A_{450}$ of inhibition group)/$A_{450}$ of control group]×100%.

3) Immuno-Fluorescence Staining:

A cell suspension of HHCC which highly expressed the HAb18G antigen was prepared. The concentration of the HHCC suspension was adjusted to $5×10^9$-$1×10^{10}$ cells/mL. HAb18 Fab was diluted with horse blood serum and then added to the HHCC suspension and incubated for 30 minutes at 4° C. Cells were washed twice, FITC conjugated rabbit anti-human IgG was then added and incubated at 4° C. for 30 minutes. After washing twice, cells were fixed and mounted and then observed under a fluorescent microscope. In this experiment, chimeric HAb18IgG was used as a positive control, PBS as blank control, and human IgG as a negative control.

2. Results 2.1 Construction of the Universal Expression Vector for Chimeric Human/Mouse Fab Antibody Using two pairs of primers, HuCH1back and HuCH1for, and HuCLback and HuCLfor respectively, the desired genes, which had the expected size, were amplified successfully. After they were cloned into the T vector, sequence analysis demonstrated that the sequences of these genes were completely identical with the sequences of known human IgG3CH1 gene and human κ light chain constant region gene. These genes were respectively 324 bp and 333 bp in length. Also correct restriction sites have been incorporated. Restriction analysis of the recombinant universal expression vector pComb3C showed that the IgG3CH1 gene and human κ light chain constant region gene have been correctly inserted into the corresponding restriction sites of the vector pComb3 (FIG. 7).

2.2 Construction of HAb18cFab Gene Expression Vector

Using two pairs of primers, HuCH1back and HuCH1for, and HuCLback and HuCLfor respectively, desired genes with expected size were amplified. The recombinant expression vector pComb3C/cFab was constructed through cleavage and ligation of the vector and the corresponding genes (FIG. 8). Restriction analysis showed that the desired gene fragments had been correctly inserted into the corresponding restriction sites of the vector pComb3C (FIG. 9). Sequence analysis showed that the heavy chain variable region (VH) sequence in the chimeric Fd and the light chain variable region (VL) sequence in the chimeric light chain were identical with the cloned sequences of the variable regions of McAb HAb18. The corresponding restriction sites were also adequately incorporated. Meanwhile, the murine VH and VL were respectively correctly ligated with human IgG3CH1 and κ light constant region through the restriction sites of EcoR V and Sal I. The open reading frame was correct.

2.3 Induced Expression and Identification of cFab

Sandwich ELISA detection showed that cFab was expressed by the recombination vector pComb3/cFab after IPTG induction (FIG. 10). Results from indirect ELISA also showed that the expressed cFab was capable of specifically binding with the extracellular domain of HAb18G (FIG. 10). The competitive ELISA further showed that the expressed cFab could competitively inhibit the binding of HAb18 with its specific antigen. The inhibition rate decreased with the decrease of the concentration of the expressed product (FIG. 11). The immuno-fluorescence staining revealed that the expressed cFab could specifically bind with a hepatocarcinoma cell line HHCC (FIG. 12A), but with a fluorescent intensity weaker than that of the positive control (FIG. 12B). No immuno-fluorescence staining was observed in a negative control (data not shown).

The invention claimed is:

1. An isolated polynucleotide coding for an anti-human hepatocarcinoma monoclonal antibody HAb 18 heavy chain variable region, having the sequence of SEQ ID NO: 1.

2. An isolated polynucleotide coding for an anti-human hepatocarcinoma monoclonal antibody HAb 18 light chain variable region, having the sequence of SEQ ID NO:2.

3. An expression vector comprising the isolated polynucleotide in claim 1 or claim 2.

4. An isolated host cell transformed or transfected by the expression vector in claim 3.

5. An isolated polynucleotide coding for a recombinant Fab, comprising the isolated polynucleotide coding for the heavy chain variable region of SEQ ID No. 1, and the light chain variable region of SEQ ID No. 2.

6. An expression vector, comprising the isolated polynucleotide coding for a recombinant Fab in claim 5, wherein the vector is pComb3/Fd-L.

7. An isolated polynucleotide coding for a chimeric human/mouse Fab, comprising the isolated polynucleotide coding for the heavy chain variable region of SEQ ID No. 1, and the isolated polynucleotide coding for the light chain variable region of SEQ ID No. 2.

8. An expression vector comprising the isolated polynucleotide coding for the chimeric human/mouse Fab in claim 7, wherein the vector is pComb3C/cFab.

* * * * *

SEQUENCE LISTING

<160> NUMBER OF SEQ ID NOS: 27

<210> SEQ ID NO 1
<211> LENGTH: 445
<212> TYPE: DNA
<213> ORGANISM: Mouse

<400> SEQUENCE: 1

```
ggggatatcc accatgaact tcgggctgag ctgggttttc atagttattc tcttaaaagg      60
tgtccagagt gaagtgaagc ttgaggagtc tggaggaggc ttggtgcaac ctggaggatc     120
catgaaactg tcttgtgttg cctctggatt cacttttagt gacgcctgga tggactgggt     180
ccgccagtct ccagagaagg gacttgagtg ggttgctgaa attagaagca aagctaataa     240
tcatgcacca tactatactg agtctgtgaa agggaggttc accatctcac gagatgattc     300
caaaagtatt atctacctgc aaatgaacaa cttaagagct gaagacactg gcatttatta     360
ctgtaccagg gatagcacgg ctacccactg gggccaaggg actctggtca ctgtctcttc     420
agctagcacg acagccccat cagtc                                           445
```

<210> SEQ ID NO 2

<211> LENGTH: 421
<212> TYPE: DNA
<213> ORGANISM: Mouse

<400> SEQUENCE: 2

```
ggggatatcc accatggact cacatactca ggtctttata tttctactgc tctgtgtgtc      60
tggtgcccat gggagtattg tgatgaccca gactcccaca ttcctggttg tatcagcagg     120
agacagggtt accataacct gcaaggccag tcagagtgtg attaatgatg tagcttggta     180
ccaacagaag ccagggcagt ctcctaaact gctgatattc tatgcatcca atcgcaacac     240
tggagttcct gatcgcttca ctggcagtgg atatgggacg gatttcactt tcaccatcag     300
cactgtgcag gctgaagacc tggcagttta tttctgtcag caggattata gtcctccatt     360
cacgttcggc tcggggacaa agctggaaat caaacgcaag tcgactgcac caactgtatc     420
c                                                                     421
```

<210> SEQ ID NO 3
<211> LENGTH: 144
<212> TYPE: PRT
<213> ORGANISM: Mouse

<400> SEQUENCE: 3

```
Met Asn Phe Gly Leu Ser Trp Val Phe Ile Val Ile Leu Leu Lys Gly
1               5                   10                  15
Val Gln Ser Glu Val Lys Leu Glu Glu Ser Gly Gly Gly Leu Val Gln
                20                  25                  30
Pro Gly Gly Ser Met Lys Leu Ser Cys Val Ala Ser Gly Phe Thr Phe
            35                  40                  45
Ser Asp Ala Trp Met Asp Trp Val Arg Gln Ser Pro Glu Lys Gly Leu
        50                  55                  60
Glu Trp Val Ala Glu Ile Arg Ser Ala Asn Asn His Ala Pro Thr Thr
65                  70                  75                  80
Thr Thr Glu Ser Val Lys Gly Arg Phe Thr Ile Ser Arg Asp Asp Ser
                85                  90                  95
Lys Ser Ile Ile Thr Leu Gln Met Asn Asn Leu Arg Ala Glu Asp Thr
            100                 105                 110
Gly Ile Thr Thr Cys Thr Arg Asp Ser Thr Ala Thr His Trp Gly Gln
        115                 120                 125
Gly Thr Leu Val Thr Val Ser Ser Ala Ser Thr Thr Ala Pro Ser Val
    130                 135                 140
```

<210> SEQ ID NO 4
<211> LENGTH: 136
<212> TYPE: PRT
<213> ORGANISM: Mouse

<400> SEQUENCE: 4

```
Met Asp Ser His Thr Gln Val Phe Ile Phe Leu Leu Leu Cys Val Ser
1               5                   10                  15
Gly Ala His Gly Ser Ile Val Met Thr Gln Thr Pro Thr Phe Leu Val
                20                  25                  30
Val Ser Ala Gly Asp Arg Val Thr Ile Thr Cys Lys Ala Ser Gln Ser
            35                  40                  45
Val Ile Asn Asp Val Ala Trp Thr Gln Gln Lys Pro Gly Gln Ser Pro
        50                  55                  60
Lys Leu Leu Ile Phe Thr Ala Ser Asn Arg Asn Thr Gly Val Pro Asp
65                  70                  75                  80
```

```
Arg Phe Thr Gly Ser Gly Thr Gly Thr Asp Phe Thr Phe Thr Ile Ser
                85                  90                  95
Thr Val Gln Ala Glu Asp Leu Ala Val Thr Phe Cys Gln Gln Asp Thr
            100                 105                 110
Ser Pro Pro Phe Thr Phe Gly Ser Gly Thr Lys Leu Glu Ile Lys Arg
        115                 120                 125
Lys Ser Thr Ala Pro Thr Val Ser
    130                 135
```

```
<210> SEQ ID NO 5
<211> LENGTH: 22
<212> TYPE: DNA
<213> ORGANISM: Mouse

<400> SEQUENCE: 5
aagtgaagct tctcgagtct gg                                              22

<210> SEQ ID NO 6
<211> LENGTH: 43
<212> TYPE: DNA
<213> ORGANISM: Mouse

<400> SEQUENCE: 6
gggatatcca ccatggagat gcgagctgtg gtcaatcgct ctt                       43

<210> SEQ ID NO 7
<211> LENGTH: 42
<212> TYPE: DNA
<213> ORGANISM: Mouse

<400> SEQUENCE: 7
ggggatatcc accatgagac ttcgggtctg agcttgggtt tt                        42

<210> SEQ ID NO 8
<211> LENGTH: 38
<212> TYPE: DNA
<213> ORGANISM: Mouse

<400> SEQUENCE: 8
ggggatatcc accatggctg tcttggggct gctcttct                             38

<210> SEQ ID NO 9
<211> LENGTH: 46
<212> TYPE: DNA
<213> ORGANISM: Mouse

<400> SEQUENCE: 9
gacactcatg gggcgtgttc gtgctagctg acaggagaca gtgtga                    46

<210> SEQ ID NO 10
<211> LENGTH: 38
<212> TYPE: DNA
<213> ORGANISM: Mouse

<400> SEQUENCE: 10
ggggatatcc accatggaga cagacacact cctgctat                             38

<210> SEQ ID NO 11
<211> LENGTH: 39
<212> TYPE: DNA
<213> ORGANISM: Mouse
```

```
<400> SEQUENCE: 11
ggggatatcc accatggatt ttcaagtgca gattttcag                              39

<210> SEQ ID NO 12
<211> LENGTH: 44
<212> TYPE: DNA
<213> ORGANISM: Mouse

<400> SEQUENCE: 12
ggggatatcc accatggaga tcacagtatc tcgggtcttt gata                        44

<210> SEQ ID NO 13
<211> LENGTH: 41
<212> TYPE: DNA
<213> ORGANISM: Mouse

<400> SEQUENCE: 13
ggatatccac catggtcccc atagctcagc ttcctcttgg t                           41

<210> SEQ ID NO 14
<211> LENGTH: 37
<212> TYPE: DNA
<213> ORGANISM: Mouse

<400> SEQUENCE: 14
ggggatatcc accatgaagt tgcctgttag gctgttg                                37

<210> SEQ ID NO 15
<211> LENGTH: 46
<212> TYPE: DNA
<213> ORGANISM: Mouse

<400> SEQUENCE: 15
ggatacagtt ggtggtgcag tcgacttacg tttgtgtttc aagctt                      46

<210> SEQ ID NO 16
<211> LENGTH: 22
<212> TYPE: DNA
<213> ORGANISM: Mouse

<400> SEQUENCE: 16
aagtgaagct tctcgagtct gg                                                22

<210> SEQ ID NO 17
<211> LENGTH: 30
<212> TYPE: DNA
<213> ORGANISM: Mouse

<400> SEQUENCE: 17
aggcttacta gtacaatccc tgggcacaat                                        30

<210> SEQ ID NO 18
<211> LENGTH: 28
<212> TYPE: DNA
<213> ORGANISM: Mouse

<400> SEQUENCE: 18
gatgtgagct cgtgatgacc cagactcc                                          28

<210> SEQ ID NO 19
<211> LENGTH: 34
<212> TYPE: DNA
<213> ORGANISM: Mouse
```

-continued

```
<400> SEQUENCE: 19
gcgccgtcta gaattaacac tcattcctgt tgaa                                34

<210> SEQ ID NO 20
<211> LENGTH: 22
<212> TYPE: DNA
<213> ORGANISM: Mouse

<400> SEQUENCE: 20
aagtgaagct tctcgagtct gg                                             22

<210> SEQ ID NO 21
<211> LENGTH: 24
<212> TYPE: DNA
<213> ORGANISM: Mouse

<400> SEQUENCE: 21
ggggatatct gcagagacag tgac                                           24

<210> SEQ ID NO 22
<211> LENGTH: 39
<212> TYPE: DNA
<213> ORGANISM: Mouse

<400> SEQUENCE: 22
ggggctcgag ttgatatctc caccaagggc ccatcggtc                           39

<210> SEQ ID NO 23
<211> LENGTH: 30
<212> TYPE: DNA
<213> ORGANISM: Mouse

<400> SEQUENCE: 23
gcatgtacta gttttgtcac aagatttggg                                     30

<210> SEQ ID NO 24
<211> LENGTH: 36
<212> TYPE: DNA
<213> ORGANISM: Mouse

<400> SEQUENCE: 24
cagatgtgag ctcagtattg tgatgaccca gactcc                              36

<210> SEQ ID NO 25
<211> LENGTH: 28
<212> TYPE: DNA
<213> ORGANISM: Mouse

<400> SEQUENCE: 25
ggggtcgacg ttttatttcc aactttgt                                       28

<210> SEQ ID NO 26
<211> LENGTH: 39
<212> TYPE: DNA
<213> ORGANISM: Mouse

<400> SEQUENCE: 26
gttccgagct caagtcgacc tgtggctgca ccatctgtc                           39

<210> SEQ ID NO 27
<211> LENGTH: 62
<212> TYPE: DNA
```

```
<213> ORGANISM: Mouse

<400> SEQUENCE: 27
gcgccgtcta gaattaacac tctcccctgt tgaagctctt tgtgacgggc gaactcaggc        60
cc                                                                      62
```